United States Patent [19]

Tsuzuki et al.

[11] Patent Number: 5,169,428
[45] Date of Patent: Dec. 8, 1992

[54] TETRAHYDROPHTHALIMIDE DERIVATIVE AND HERBICIDE COMPOSITION CONTAINING SAME

[75] Inventors: Kenji Tsuzuki, Sinnanyooshi; Sinzo Someya, Tokorozawa; Seigo Koura, Nerima; Yasuaki Hanasaki, Sinnanyooshi; Mikio Ito, Tokuyama; Hiroyuki Watanabe, Sinnanyooshi, all of Japan

[73] Assignee: Tosoh Corporation, Ya Maguchi, Japan

[21] Appl. No.: 726,724

[22] Filed: Jul. 1, 1991

Related U.S. Application Data

[63] Continuation of Ser. No. 291,759, Dec. 29, 1989, abandoned.

[30] Foreign Application Priority Data

Dec. 30, 1987 [JP] Japan ................. 62-334000
Dec. 31, 1987 [JP] Japan ................. 62-336451
Sep. 8, 1988 [JP] Japan ................. 63-225463
Sep. 8, 1988 [JP] Japan ................. 63-225465
Sep. 19, 1988 [JP] Japan ................. 63-234258

[51] Int. Cl.$^5$ ............... C07D 209/48; C07D 413/10; A01N 43/82; A01N 43/38
[52] U.S. Cl. ........................... 71/92; 71/95; 548/131; 548/465; 548/513
[58] Field of Search ................. 548/131, 513, 465; 71/92, 95

[56] References Cited

U.S. PATENT DOCUMENTS

| | | | |
|---|---|---|---|
| H531 | 10/1988 | Ray | 71/86 |
| 4,431,822 | 2/1984 | Nagano et al. | 548/513 |
| 4,484,940 | 11/1984 | Nagano et al. | 548/513 |
| 4,484,941 | 11/1984 | Nagano et al. | 548/513 |
| 4,670,046 | 11/1987 | Nagano et al. | 548/513 |

FOREIGN PATENT DOCUMENTS

| | | | |
|---|---|---|---|
| 0049508 | 4/1982 | European Pat. Off. | |
| 0068822 | 1/1983 | European Pat. Off. | |
| 0150064 | 7/1985 | European Pat. Off. | |
| 0061741 | 9/1985 | European Pat. Off. | 548/513 |
| 0172306 | 2/1986 | European Pat. Off. | |
| 0083055 | 9/1986 | European Pat. Off. | 548/513 |
| 3013162 | 10/1980 | Fed. Rep. of Germany . | |
| 2119703 | 7/1972 | France . | |
| 8704049 | 7/1987 | PCT Int'l Appl. . | |
| 8707602 | 12/1987 | PCT Int'l Appl. . | |

OTHER PUBLICATIONS

Chemical Abstracts, vol. 102, No. 9, Mar. 4, 1985, p. 584, column 1, Abstract No. 78702d.
Chemical Abstracts, vol. 101, No. 19, Nov. 5, 1984, p. 687, column 1, Abstract No. 171089u.
Chemical Abstracts, vol. 97, No. 25, Dec. 20, 1982, p. 834, column 2, Abstract No. 215986q.

Primary Examiner—Robert Gerstl
Attorney, Agent, or Firm—Nixon & Vanderhye

[57] ABSTRACT

Disclosed is a tetrahydrophthalimide derivative of the formula (I):

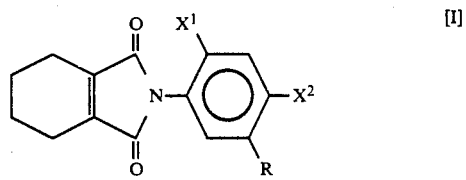

wherein $X^1$ and $X^2$, the same or different, represent halogen, hydrogen or trifluoromethyl; R represents

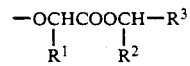

(wherein $R^1$ and $R^2$, the same or different, represent hydrogen or methyl, $R^3$ represents 2-tetrahydrofurfuryl or 3-methyl-1,2,4-oxadiazol-5-yl),

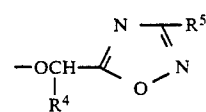

(wherein $R^4$ is hydrogen or methyl, $R^5$ is methyl or benzyl),

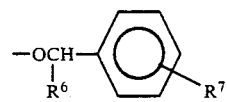

(wherein $R^6$ represents hydrogen or methyl, $R^7$ is halogen or $C_1$–$C_4$ alkyl),

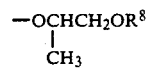

(wherein $R^8$ is hydrogen, acyl or arylalkyl), cyano, or —$CH_2OR^9$ (wherein $R^9$ is hydrogen, acetyl, halophenyl, $C_1$–$C_4$ tetrahydrophthalimide derivative of the present invention is useful as a herbicide.

8 Claims, No Drawings

TETRAHYDROPHTHALIMIDE DERIVATIVE AND HERBICIDE COMPOSITION CONTAINING SAME

This is a continuation of application Ser. No. 07/291,759, filed Dec. 29, 1988, now abandoned.

BACKGROUND OF THE INVENTION

I. Field of the Invention

This invention relates to a novel tetrahydrophthalimide derivative which has excellent herbicidal activity and selectivity.

II. Description of the Related Art

The herbicidal activity of the tetrahydrophthalimide derivatives is well-known in the art. For example, Japanese Patent Disclosure (Kokai) Nos. 163365/82 and 110566/83 disclose the tetrahydrophthalimide derivatives having herbicidal activity, which are represented by the formula [A] and [B], respectively.

However, some of the known tetrahydrophthalimide derivatives do not have satisfactory herbicidal activity. The other known tetrahydrophthalimide derivatives do not have satisfactory selectivity. That is, when the herbicide comprising the derivative is applied to the crops and weeds, not only the weeds, but also the crops may be damaged. Thus, the safety of the herbicide is not good.

SUMMARY OF THE INVENTION

Accordingly, the object of the present invention is to provide a novel tetrahydrophthalimide derivative which has a high herbicidal activity and selectivity.

Another object of the present invention is to provide a herbicide composition having a high herbicidal activity and selectivity.

The present inventors intensively studied to find that a specific tetrahydrophthalimide derivative has a high herbicidal activity and selectivity to complete the present invention.

That is, the present invention provides a novel tetrahydrophthalimide derivative of the formula [I]:

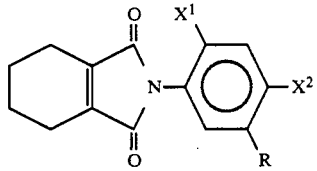

wherein $X^1$ and $X^2$, the same or different, represent halogen, hydrogen or trifluoromethyl; R represents

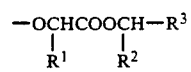

(wherein $R^1$ and $R^2$, the same or different, represent hydrogen or methyl, $R^3$ represents 2-tetrahydrofurfuryl or 3-methyl-1,2,4-oxadiazole-5-yl),

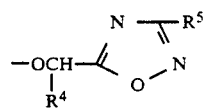

(wherein $R^4$ is hydrogen or methyl, $R^5$ is methyl or benzyl),

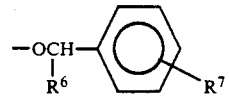

(wherein $R^6$ represents hydrogen or methyl, $R^7$ is halogen or $C_1$-$C_4$ alkyl),

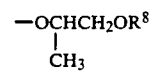

(wherein $R^8$ is hydrogen, acyl or arylalkyl), cyano, or —$CH_2OR^9$ (wherein $R^9$ is hydrogen, acetyl, halophenyl, $C_1$-$C_4$ alkyl which may be substituted with alkoxycarbonyl).

By the present invention, a novel tetrahydrophthalimide derivative with high herbicidal activity and selectivity was provided As will be clearly demonstrated in the Examples later described, the tetrahydrophthalimide derivative of the present invention has a high herbicidal activity while it does not substantially damage the useful crops such as wheat, corn and soybean. Thus, it can be used safely for the inhibition of the growth of weeds in the field of such crops.

DETAILED DESCRIPTION OF THE PREFERRED EMBODIMENTS

Preferred examples of the tetrahydrophthalimide derivative of the present invention represented by the formula [I] above include those represented by the following formula [II]:

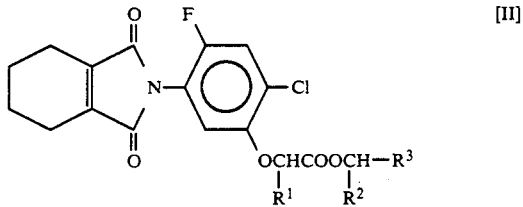

wherein $R^1$ and $R^2$, the same or different, represent hydrogen or methyl, $R^3$ represents 2-tetrahydrofurfuryl or 3-methyl-1,2,4-oxadiazol-5-yl.

Preferred and non-limiting specific examples of the tetrahydrophthalimide derivative represented by the formula [II] include those summarized in Table 1 below.

TABLE 1

| Compound No. | $R^1$ | $R^2$ | $R^3$ |
|---|---|---|---|
| 1 | $CH_3$ | $CH_3$ | 3-methyl-1,2,4-oxadiazol-5-yl |
| 2 | H | $CH_3$ | 3-methyl-1,2,4-oxadiazol-5-yl |
| 3 | $CH_3$ | H | 2-tetrahydrofuryl |

TABLE 1-continued

| Compound No. | $R^1$ | $R^2$ | $R^3$ |
|---|---|---|---|
| 4 | H | H | 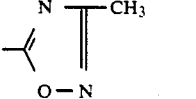 |

Second group of the preferred examples of the tetrahydrophthalimide derivative of the present invention represented by the formula [I] include those represented by the following formula [III]:

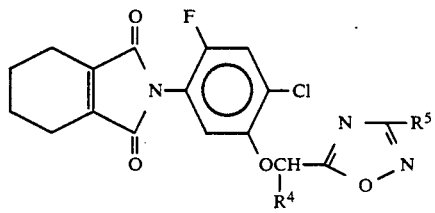

[III]

wherein $R^4$ is hydrogen or methyl, $R^5$ is methyl or benzyl.

Preferred and non-limiting specific examples represented by the formula [III] include those summarized in Table 2 below.

TABLE 2

| Compound No. | $R^4$ | $R^5$ |
|---|---|---|
| 5 | $CH_3$ | $CH_3$ |
| 6 | H | $CH_2$–⌬ |
| 7 | $CH_3$ | $CH_2$–⌬ |

Third group of the preferred examples of the tetrahydrophthalimide derivative of the present invention represented by the formula [I] include those represented by the following formula [IV]:

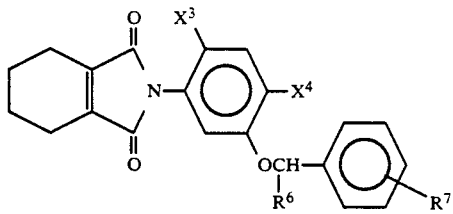

[IV]

wherein $X^3$ and $X^4$, the same or different, represent halogen, $R^6$ represents hydrogen or methyl, $R^7$ represents halogen or $C_1$–$C_4$ alkyl.

Preferred and non-limiting specific examples represented by the formula [IV] include those summarized in Table 3 below.

TABLE 3

| Compound No. | $R^6$ | $X^3$ | $X^4$ | $R^7$ |
|---|---|---|---|---|
| 8 | H | H | Cl | — |
| 9 | H | H | Cl | 2-F |
| 10 | H | H | Cl | 4-F |
| 11 | H | F | Cl | — |
| 12 | H | F | Cl | 2-F |
| 13 | H | F | Cl | 2-$CH_3$ |
| 14 | H | Cl | Cl | 2-F |
| 15 | H | Br | Cl | — |
| 16 | H | Br | Cl | 2-F |
| 17 | $CH_3$ | F | Cl | — |
| 18 | $CH_3$ | Cl | Cl | — |

Fourth group of preferred examples of the tetrahydrophthalimide derivative of the present invention is represented by the following formula [V]:

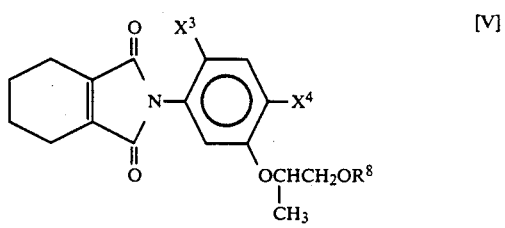

[V]

wherein $X^3$ and $X^4$, the same or different, represent halogen, $R^8$ represents hydrogen, acyl or arylalkyl.

Preferred and non-limiting specific examples of those represented by the formula [V] include those summarized in Table 4 below.

TABLE 4

| Compound No. | $X^3$ | $X^4$ | $R^8$ |
|---|---|---|---|
| 19 | F | Cl | H |
| 20 | F | Cl | $COCH_3$ |
| 21 | F | Cl | $CH_2$–⌬ |
| 22 | Cl | Cl | $CH_2$–⌬(F) |
| 23 | Cl | Cl | H |

Fifth group of preferred examples of the tetrahydrophthalimide derivative of the present invention is represented by the following formula [VI]:

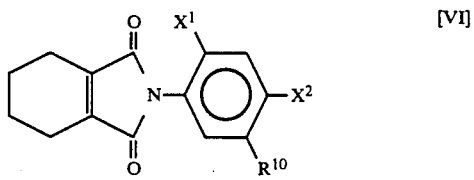

[VI]

wherein $X^1$ and $X^2$, the same or different, represent hydrogen, halogen or trifluoromethyl, $R^{10}$ represents cyano or —$CH_2OR^9$ (wherein $R^9$ represents hydrogen, acetyl, halophenyl, $C_1$–$C_4$ alkyl which may be substituted with alkoxycarbonyl).

Preferred and non-limiting specific examples of those represented by the formula [VI] are summarized in Table 5 below.

TABLE 5

| Compound No. | $X^1$ | $X^2$ | $R^8$ |
|---|---|---|---|
| 24 | H | Cl | $CH_2OH$ |
| 25 | H | Cl | $CH_2OCOCH_3$ |
| 26 | H | Cl | $CH_2O\text{-}C_6H_4F$ |
| 27 | H | Cl | $CH_2OCH(CH_3)COOC_2H_5$ |
| 28 | H | Cl | CN |
| 29 | H | Br | CN |
| 30 | F | Cl | CN |
| 31 | H | $CF_3$ | CN |

The tetrahydrophthalimide derivative of the present invention may be prepared by various processes. More particularly, those represented by the formula [II] may be prepared according to the following Equation 1:

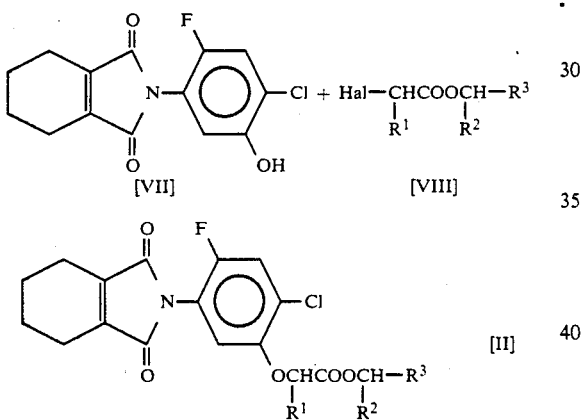

In the above Equation 1, Hal represents halogen (Hal means halogen also in the subsequent formulae), $R^1$, $R^2$ and $R^3$ represent the same meaning as in formula [II].

The reaction may be conducted in an appropriate solvent under the presence of a base at a temperature ranging from 0° C.–150° C., preferably 20°–100° C. for several minutes to 48 hours.

Preferred examples of the solvents which may be employed in the reaction may include ketones such as acetone and methyl ethyl ketone; aromatic hydrocarbons such as benzene and xylene; ethers such as ethyl ether, tetrahydrofuran and dioxane; halogenated hydrocarbons such as chlorobenzene, chloroform, tetrachloromethane and dichloroethane; tertiary amines such as triethylamine, pyridine and dimethylaniline; and polar solvents such as acetonitrile, dimethylformamide, dimethylsulfoxide and hexamethylphosphoramide.

Preferred examples of the bases which may be employed in the reaction may include organic bases such as triethylamines, 1,3-diazabicyclo[5,4,0]undec-7-ene and dimethylaniline; alkali metal hydroxide such as sodium hydroxide; alkaline earth metal hydroxides such as calcium hydroxide; alkaline metal salts of carbonic acid such as sodium carbonate, potassium carbonate, sodium hydrogen carbonate and potassium hydrogen carbonate; and metal hydrides such as sodium hydride.

Typically, 1–5 equivalents of the halogen compound [VIII] and 1–10 equivalents of the base are reacted with 1 equivalent of the compound [VII].

The tetrahydrophthalimide derivatives represented by the formula [III] may be prepared according to the following Equation 2 or 3:

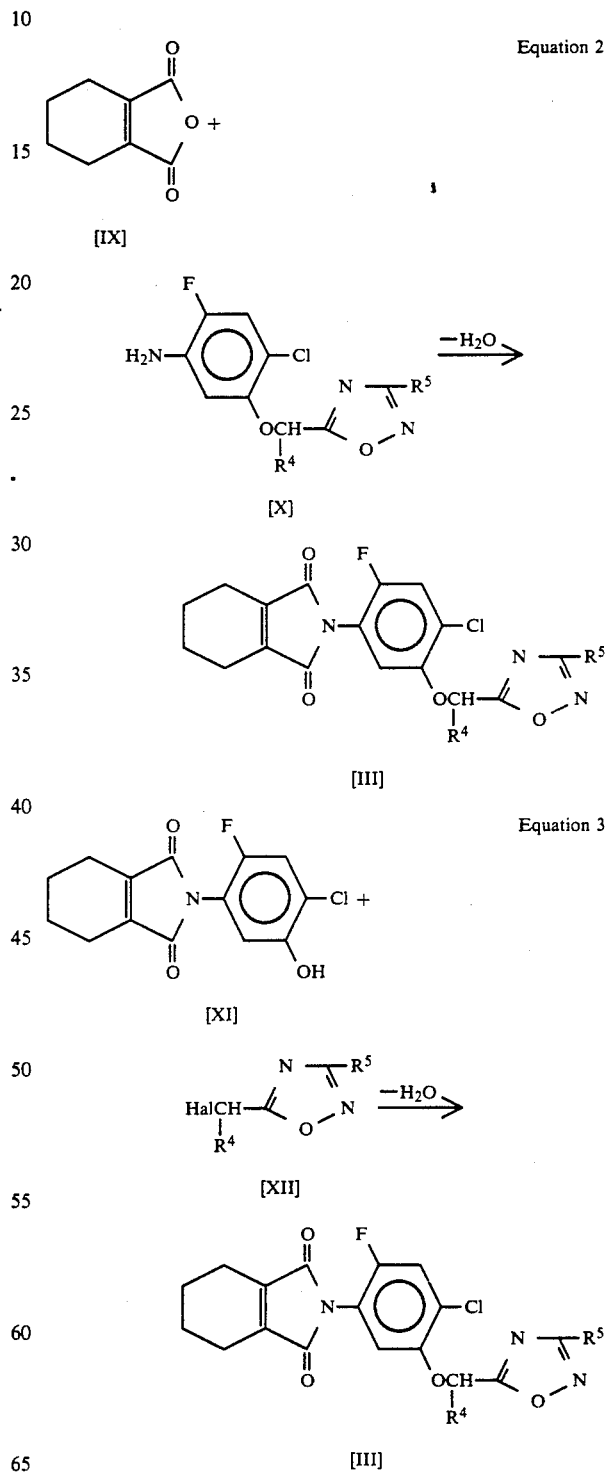

The reaction may be conducted in the same conditions as in Equation 1. The solvents and bases which are preferred in Equation 1 are also preferred in these reactions.

Typically, 1-5 equivalents of the compound [X] or [XII] and 1-10 equivalents of the base are reacted with 1 equivalent of the compound [IX] or [XI].

The tetrahydrophthalimide derivatives represented by the formula [IV] may be prepared according to the following Equation 4 or 5:

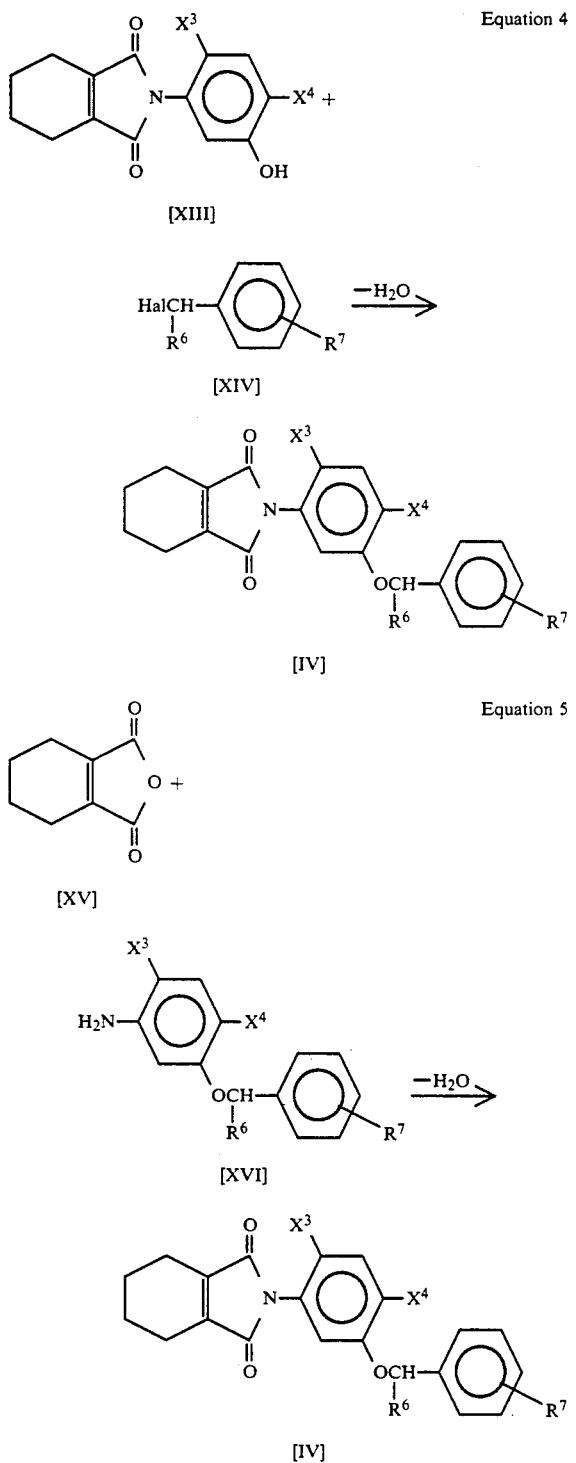

preferred in Equation 1 are also preferred in these reactions.

Typically, 1-5 equivalents of the compound [XIV] or [XVI] and 1-10 equivalents of the base are reacted with 1 equivalent of the compound [XIII] or [XV].

The tetrahydrophthalimide derivatives represented by the formula [V] may be prepared according to the following Equation 6:

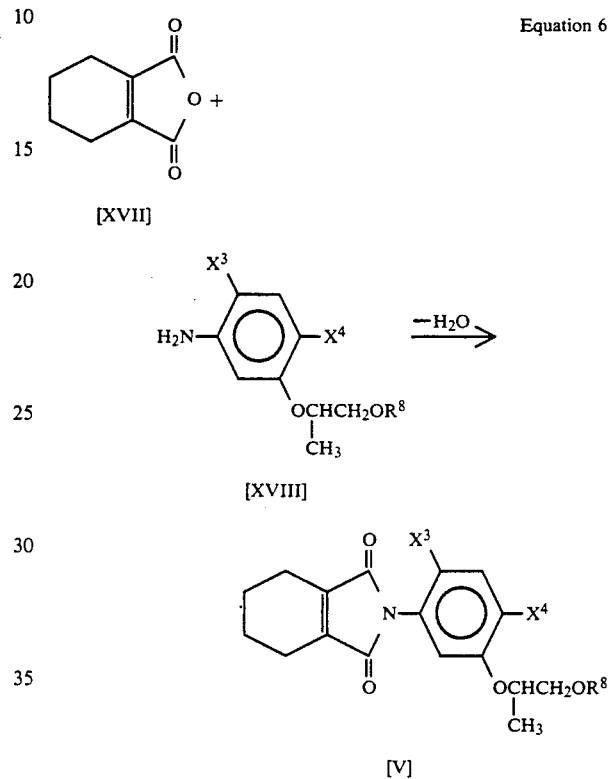

The reaction may be conducted in the same conditions as in Equation 1. The solvents and bases which are preferred in Equation 1 are also preferred in these reactions.

Typically, 1-5 equivalents of the compound [XVIII] and 1-10 equivalents of the base are reacted with 1 equivalent of the compound [XVII].

The tetrahydrophthalimide derivatives represented by the formula [VI] may be prepared according to the following Equation 7 or 8:

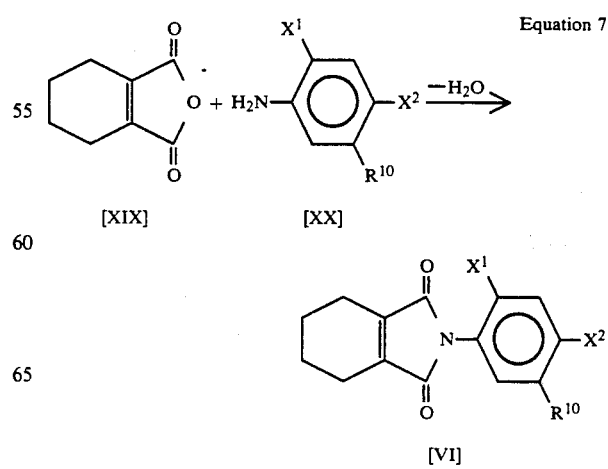

The reaction may be conducted in the same conditions as in Equation 1. The solvents and bases which are Equation 8

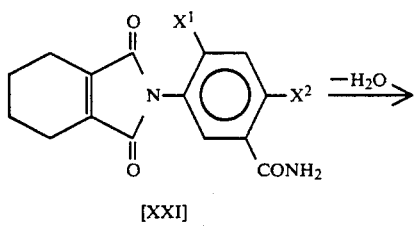

[XXI]

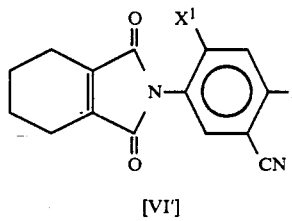

[VI']

The reaction according to the Equation 7 may be conducted in the same conditions as in Equation 1. The solvents and bases which are preferred in Equation 1 are also preferred in these reactions.

Typically, 1-5 equivalents of the compound [XX] and 1-10 equivalents of the base are reacted with 1 equivalent of the compound [XIX].

The reaction according to the Equation 8 may be conducted in the presence or absence of a solvent, in the presence of a catalyst, at a temperature ranging from $-20°$ C. to $300°$ C., preferably $0°$ C.-$200°$ C. for several minutes to 48 hours.

The solvents preferred in the reaction of Equation 1 are also preferred in the reaction of Equation 8.

Preferred examples of the catalysts which may be employed in the reaction of Equation 8 may include chlorinating agents or dehydrants such as phosphorus oxychloride, phosphorus pentoxide, phosphorus pentachloride, phosphorus trichloride and sulfuryl chloride; dehydrating reagents such as triethylamine, chloroformate, DCC and anhydrous acetic acid.

The amount of the catalyst is usually 1 to 100 equivalents with respect to 1 equivalent of the compound [XXI].

The present invention further provides a herbicide composition comprising the tetrahydrophthalimide derivative of the present invention as effective ingredient in an agriculturally acceptable carrier. The herbicide composition of the present invention is effective for inhibiting the growth of various weeds growing in paddy field including the weeds belonging to the Gramineae such as barnyardgrass; broadleaved weeds such as Falsepinpernel, spindle-flowered rotala, water starwart and monochoria; and those belonging to the family cyperaceae such as small flower umbrellaplant, slender spikerush and water nutgrass. Further, the tetrahydrophthalimide derivative of the present invention is particularly effective for inhibiting the growth of weeds growing in fields, such as mustard, virginia pepperweed, catchweed badstraw, Kinutaso (Galium kinuta), chick weed, Common lambsquaters, nottle (Utrica Thunbergiana), Common groundsel, Alender amaranth, Cocklebur, Pale smartweed, Velvetleaf and barynard grass. The herbicide composition of the present invention does not substantially damage the crops belonging to Family Graminae such as corn, rice and wheat, so that it is highly safe.

The agriculturally acceptable carriers per se which may be employed in the present invention are well-known in the art, and either liquid carrier or solid carrier may be employed. Preferred examples of the liquid carrier or diluent may include water, hydrocarbons, ethers, alkoxy alcohols, ketones, esters, amides and sulfoxides. Preferred examples of the solid carriers or extender may include powder and granules of inorganic materials such as slaked lime, gypsum, calcium carbonate, silica, pearlite, pumice, diatomaceous earth, alumina, zeolite and clay minerals (e.g., talc, vermiculite and kaolinite); powder and granules of plant products such as starch, cereals and glucose; and powder and granules of synthetic products such as phenol resins, carbon resins and vinyl chloride resins. The concentration of the active ingredient in the composition is not critical and may usually be 0.1% by weight to 90% by weight, preferably 1% by weight to 80% by weight.

If necessary, the herbicide composition of the present invention may contain a surfactant. The surfactants are well-known and widely used in the art. Preferred examples of the surfactants include anion surfactants such as alkylsulfate esters, arylsulfonic acids, salts of succinic acid and polyethyleneglycolalkylaryl ethers and ester salts of sulfuric acid; cation surfactants such as alkylamines and polyoxyethylenealkylamines; non-ionic surfactants such as polyoxyethyleneglycol ethers and polyol esters; and ampholytic surfactants. If desired, the herbicide composition of the present invention may contain other additives which are often employed in herbicide compositions. The examples of such additives may include stabilizers, dispersion stabilizers, fixing agents, effect prolongers and synergists. The composition may also contain other herbicides, bacteriocides, fungicides and the like.

The herbicide composition may be formulated to an emulsifiable concentrate, wettable powder, aqueous solution, oily solution, granule or powder. The methods of formulating herbicide composition are well-known in the art.

Specific non-limiting examples of the preferred formulations of the present invention will now be described. In the following examples, all parts are based on weight.

| Formulation 1 (Emulsifiable Concentrate) | |
|---|---|
| Compound of the present invention: | 20 parts |
| xylene: | 60 parts |
| Solpol (a surfactant commercially available from Toho Kogaku Kogyo) | 20 parts |

This formulation may be prepared by uniformly mixing the components.

| Formulation 2 (Wettable Powder) | |
|---|---|
| Compound of the present invention | 20 parts |
| White Carbon | 10 parts |
| Zeaklite | 65 parts |
| Solpol (a surfactant commercially available from Toho Kogaku Kogyo) | 5 parts |

This composition may be prepared by mixing and pulverizing the components.

| Formulation 3 (Wettable Powder) | |
|---|---|
| Compound of the present invention | 10 parts |

-continued

| Formulation 3 (Wettable Powder) | |
|---|---|
| Zeaklite | 87 parts |
| Neoplex Powder (commercially available from Kao corporation) | 1.5 parts |
| Solpol (a surfactant commercially available from Toho Kogaku Kogyo) | 1.5 parts |

This composition may be prepared by mixing and pulverizing the components.

The amount of the compound of the present invention to be applied to the field varies depending on the formulation of the composition, method of application, species and stage of growth of the weeds. Typically, the amount to be applied may be 0.05 kg/ha to 10 kg/ha, preferably 0.1 kg/ha to 5 kg/ha in terms of the weight of the active compound of the present invention.

The herbicide composition of the present invention may directly be applied to the leaves or stems of weeds or to the field before the germination of the weeds. The herbicide composition may be applied as it is or may be diluted with water before use.

The invention will now be described by way of the examples thereof. It should be understood that the examples are presented for the illustration purpose only and should not be interpreted any restrictive way.

EXAMPLE 1

Preparation of N-[4-chloro-2-fluoro-5-(1-tetrahydrofurfuryloxycarbonyl)-ethoxyphenyl-2,4,5,6 -tetrahydrophthalimide (Compound No. 3 (see Table 1)

To 20 ml of acetonitrile containing 0.59 g of N-(4-chloro-2-fluoro-5-hydroxyphenyl)3,4,5,6-tetrahydrophthalimide and 0.30 g of anhydrous potassium carbonate, was added 0.30 g of 2-chloropropionic acid tetrahydrofurfuryl ester in 10 ml of acetonitrile and the resulting mixture was heated to reflux for 5 hours. After allowing to cool, water was added to the mixture and the resulting mixture was extracted with ether. After drying the extract, the solvent was evaporated under reduced pressure and the obtained residue was subjected to a column chromatography (silica gel) to obtain 0.65 g of oily product. The eluant employed in the column chromatography was chloroform/ethyl acetate=10/1 (v/v).

$^1$H-NMR (60 MHz, CDCl$_3$ solvent) δppm 1.5–1.9 (m, 11H), 2.1–2.5 (m, 4H), 3.4–4.3 (m, 5H), 4.76 (q, J=7 Hz, 1H), 6.86 (dd, J=1.5, 6 Hz, 1H), 7.28 (d, J=9 Hz, 1H)

Refractive Index (d$_D^{25}$): 1.5448

EXAMPLE 2

Preparation of Compound No. 1 (Table 1)

The same operation as in Example 1 was repeated except that a halogen compound [VIII]](see Equation 1) having methyl groups as R$^1$ and R$^2$, and 3-methyl-1,2,4-oxadiazol-5-yl group as R$^3$ was used to obtain the Compound No. 1.

$^1$H-NMR (60 mHz, CDCl$_3$ solvent) δppm 1.5–2.0 (m, 10H), 2.2–2.6 (m, 7H), 4.83 (q, J=7 Hz, 1H), 6.05 (q, J=7 Hz, 1H), 6.81 (t, J=6 Hz, 1H), 7.25 (d, J=9 Hz, 1H)

Refractive Index (n$_D^{25}$): 1.5382

EXAMPLE 3

Preparation of Compound No. 2 (Table 1)

The same operation as in Example 1 was repeated except that a halogen compound [VIII] (see Equation 1) having hydrogen as R$^1$ and methyl group as R$^2$, and 3-methyl-1,2,4-oxadiazol-5-yl group as R$^3$ was used to obtain the Compound No. 2.

$^1$H-NMR (60 MHz, CDCl$_3$ solvent) δppm 1.70 (d, J=7 Hz, 3H), 1.6–2.0 (m, 4H), 2.36 (s, 3H), 2.2–2.6 (m, 4H), 4.76 (s, 2H), 6.10 (q, J=7 Hz, 1H), 6.83 (d, J=6 Hz, 1H), 7.25 (d, J=9 Hz, 1H)

Refractive Index (n$_D^{25}$): 1.5503

EXAMPLE 4

Preparation of Compound No. 4 (Table 1)

The same operation as in Example 1 was repeated except that a halogen compound [VIII] (see Equation 1) having hydrogen as R$^1$ and R$^2$, and 3-methyl-1,2,4-oxadiazol-5-yl group as R$^3$ was used to obtain the Compound No. 4.

$^1$H-NMR (60 MHz, CDCl$_3$ solvent) δppm 1.5–1.9 (m, 4H0, 2.30 (s, 3H), 2.1–2.5 (m, 4H), 4.75 (s, 2H), 5.30 (s, 2H), 6.80 (d, J=6 Hz, 1H), 7.20 (d, J=9 Hz, 1H)

Refractive Index (n$_D^{25}$): 1.5407

EXAMPLE 5

Test for Evaluation of Effectiveness in Growth Inhibition by Foliage Treatment

Field soil was packed in a plastic vat sizing 22 cm×16 cm and seeds of wheat (*Triticum aestivum*), corn (*Zea mays*) and soybean (*Glycine max*) were sown. The field soil was covered with soil of about 1 cm thickness which contains seeds of weeds, i.e., barnyardgrass (*Echinochloa crus-galli*), Velvetleaf, Slender amaranth, Cocklebur and Pale smartweed. When the barnyardgrass grew to have 2–2.5 leaves, each of the Compound Nos. 1–3 of the present invention was applied in the amount shown in Table 6 below. Further, for comparison, the compound of the formula [A] disclosed in Japanese Patent Disclosure (Kokai) No. 163365/82 (comparative compound A) and the compound of the formula [B] disclosed in Japanese Patnt Disclosure (Kokai) No. 110566/83 (comparative compound B) were applied separately. After 14 days from the application of the herbicide, the conditions of the growth of the weeds and the crops were observed. The results are shown in Table 6. The herbicidal effectiveness was rated in 6 ranks as follows:

Rank 0: percent growth inhibition of 0–9%
Rank 1: percent growth inhibition of 10–29%
Rank 2: percent growth inhibition of 30–49%
Rank 3: percent growth inhibition of 50–69%
Rank 4: percent growth inhibition of 70–89%
Rank 5: percent growth inhibition of 90–100%

TABLE 6

| Compound No. | Rate (a.i. g/10a) | Herbicidal Effectiveness | | | | | Phytotoxicity | | |
| | | Barnyard-grass | Pale smartweed | Slender amaranth | Cocklebur | Velvetleaf | Wheat | Corn | Soybean |
|---|---|---|---|---|---|---|---|---|---|
| 1 | 60 | 1 | 5 | 5 | 5 | 5 | 0 | 0 | 0 |
|   | 125 | 1 | 5 | 5 | 5 | 5 | 0 | 0 | 0 |
| 2 | 60 | 0 | 5 | 5 | 5 | 5 | 0 | 0 | 0 |
|   | 125 | 3 | 5 | 5 | 5 | 5 | 0 | 0 | 0 |

TABLE 6-continued

| Compound No. | Rate (a.i. g/10a) | Herbicidal Effectiveness | | | | | Phytotoxicity | | |
|---|---|---|---|---|---|---|---|---|---|
| | | Barnyard-grass | Pale smartweed | Slender amaranth | Cocklebur | Velvetleaf | Wheat | Corn | Soybean |
| 3 | 60 | 4 | 2 | 5 | 5 | 5 | 0 | 0 | 0 |
| | 125 | 4 | 5 | 5 | 5 | 5 | 0 | 0 | 0 |
| Comparative Compound A | 60 | 2 | 5 | 5 | 5 | 5 | 2 | 2 | 4 |
| | 125 | 4 | 5 | 5 | 5 | 5 | 3 | 2 | 5 |
| Comparative Compound B | 60 | 5 | 5 | 5 | 5 | 5 | 0 | 2 | 2 |
| | 125 | 5 | 5 | 5 | 5 | 5 | 2 | 2 | 3 |

EXAMPLE 6

Preparation of
N-[4-chloro-2-fluoro-5-{(3-methyl-1,2,4-oxadiazo-5-yl)-1-ethyloxy}phenyl]-3,4,5,6-tetrahydrophthalimide
(Compound No. 5, (Table 2))

To 50 ml of acetonitrile, 0.6 g of 3-methyl-5-(chloroethyl)-1,2,4-oxadiazole, 1.12 g of N-(4-chloro-2-fluoro-5-hydroxyphenyl)-3,4,5,6-tetrahydrophthalimide and 0.58 g of potassium carbonate were added and the mixture was heated to reflux for 16 hours. After the reaction mixture was allowed to cool, inorganic materials were removed by filtration and acetonitrile was evaporated. The residue was purified by column chromatography (silica gel) to obtain 0.72 g of the desired product. The eluant employed in the column chromatography was benzene/ethyl acetate=10/1 (v/v).

$^1$H-NMR (60 MHz, CDCl$_3$ solvent) δppm 1.83 (d, J=7 Hz, 3H), 1.6-2.0 (m, 4H), 2.40 (s, 3H), 2.2-2.6 (m, 4H), 5.47 (q, J=7 Hz, 1H), 6.90 (d, J=6 Hz, 1H) 7.24 (d, J=9 Hz, 1H)
m.p.: 95°-97.5° C.

EXAMPLE 7

Preparation of
N-[4-chloro-2-fluoro-5-{(3-benzyl-1,2,4-oxadiazo-5-yl)methyloxy}phenyl]-3,4,5,6-tetrahydrophthalimide
(Compound No. 6, (Table 2))

To 50 ml of acetic acid, 1.67 g of 4-chloro-2-fluoro-5-(3-benzyl-1,2,4-oxadiazol-5-yl)methyloxyaniline and 0.76 g of 3,4,5,6-tetrahydrophthalic anhydride were added, and the mixture was heated to reflux for 16 hours under stirring The reaction mixture was then concentrated under reduced pressure and under heat, and the residue was purified by column chromatography (silica gel) to obtain 1.73 g of the desired product. The eluant employed in the column chromatography was benzene/ethyl acetate=10/1 (v/v).

$^1$H-NMR (60 MHz CDCl$_3$ solvent) δppm 1.4-1.9 (m, 4H, 2.0-2.5 (m, 4H), 4.42 (s, 2H), 5.03 (s, 2H), 5.03 (s, 2H), 6.80 (d, J=6 Hz, 1H), 6.9-7.3 (broad s, 6H)

Refractive Index ($n_D{}^{25}$) 1.5761

EXAMPLE 8

Preparation of Compound No. 7 (Table 2)

The same operation as in Example 7 was repeated except that the compound [X] in Equation 2 had methyl group as R$^4$ to obtain the Compound No. 7.

$^1$H-NMR (60 MHz, CDCl$_3$ solvent δppm 1.83 (d, J=7 Hz, 3H), 1.6-2.0 (m, 4H), 2.2-2.6 (m, 4H), 4.11 (s, 2H), 5.43 (q, J=7 Hz, 1H), 6.88 (d, J=6 Hz, 1H), 7.1-7.4 (m, 6H)

Refractive Index ($n_D{}^{25}$) 1.5708

EXAMPLE 9

Test for Evaluation of Effectiveness in Growth Inhibition by Foliage Treatment

The same procedure as in Example 5 was repeated except that the compounds tested were Compound Nos. 5-7. Further, for comparison, 5-[2-chloro-4-trifluoromethyl-phenoxy]-2-nitro-benzoic acid (Comparative Compound C) and the Comparative Compound A described in Example 5 were also tested. The results are shown in Table 7 below.

TABLE 7

| Compound No. | Rate (a.i. g/10a) | Herbicidal Effectiveness | | | | | Phytotoxicity | | |
|---|---|---|---|---|---|---|---|---|---|
| | | Barnyard-grass | Pale smartweed | Slender amaranth | Cocklebur | Velvetleaf | Wheat | Corn | Soybean |
| 5 | 15 | 3 | 5 | 5 | 5 | 5 | 0 | 0 | 0 |
| | 30 | 4 | 5 | 5 | 5 | 5 | 0 | 0 | 0 |
| 6 | 15 | 3 | 5 | 5 | 5 | 5 | 0 | 0 | 0 |
| | 30 | 5 | 5 | 5 | 5 | 5 | 0 | 0 | 0 |
| 7 | 15 | 4 | 5 | 5 | 5 | 5 | 0 | 0 | 0 |
| | 30 | 4 | 5 | 5 | 5 | 5 | 0 | 0 | 0 |
| Comparative Compound C | 15 | 0 | 5 | 5 | 4 | 3 | 0 | 0 | 3 |
| | 30 | 3 | 5 | 5 | 4.5 | 4.5 | 2 | 2 | 4 |
| Comparative Compound A | 15 | 0 | 5 | 4.5 | 4.5 | 5 | 0 | 0 | 4.5 |
| | 30 | 0 | 5 | 5 | 5 | 5 | 1 | 1 | 5 |

EXAMPLE 10

Preparation of
N-(5-benzyloxy-4-chlorophenyl-3,4,5,6-tetrahydrophthalimide (Compound No. 8 (Table 3))

To 50 ml of acetonitrile, 0.55 g of N-(4-chloro-5-hydroxyphenyl)-3,4,5,6-tetrahydrophthalimide, 0.38 g of benzyl bromide and 0.27 g of potassium carbonate were added and the mixture was heated to reflux under stirring After cooling, the inorganic materials were removed by filtration and the solvent was evaporated under reduced pressure. The residue was purified by column chromatography (silica gel, benzene/ethyl acetate=10/1 (v/v)) to obtain 0.6 g of the desired product.

Refractive Index $n_D{}^{25}$: 1.5909

| | Element Analysis | | |
|---|---|---|---|
| | C | H | N |
| Found (%) | 68.83 | 4.97 | 3.82 |
| Calcd. (%) | 68.57 | 4.93 | 3.80 |

$^1$H-NMR (CDCl$_3$, δppm) 1.80 (mc, 4H), 2.40 (mc, 4H), 4.92 (s, 2H), 7.20 (mc, 8H)

EXAMPLE 11

Preparation of N-(2,4-dichloro-5-(2-fluorophenyloxy)phenyl-3,4,5,6-tetrahydrophthalimide (Compound No. 14 (Table 3))

To 50 ml of acetic acid, 0.43 g of 3,4,5,6-tetrahydrophthalic anhydride and 0.80 g of 2,4-dichloro-5-aminophenyl-2'-fluorobenzyl ether were added and the mixture was heated to reflux for 16 hours under stirring. After cooling, the solvent was evaporated under reduced pressure and the residue was purified by column chromatography (silica gel, benzene/ethyl acetate=10/1 (v/v)) to obtain 0.7 g of the desired product.
m.p.: 106°–108.5° C.

| | Element Analysis | | |
|---|---|---|---|
| | C | H | N |
| Found (%) | 59.8 | 3.81 | 3.36 |
| Calcd. (%) | 60.01 | 3.83 | 3.33 |

$^1$H-NMR (CDCl$_3$, δppm) 1.70 (mc, 4H), 2.33 (mc, 4H), 5.07 (s, 3H), 7.22 (mc, 6H)

EXAMPLE 12

Preparation of Compound No. 9

To 50 ml of acetonitrile, 0.43 g of N-(4-chloro-5-hydroxyphenyl)-3,4,5,6-tetraphydrophthalimide, 0.3 g of 2-fluoro-benzyl bromide and 0.21 g of potassium carbonate were added and the same procedure as in Example 10 was followed to obtain 0.62 g of the Compound No. 9.
m.p.: 88.5°–91° C.

| | Element Analysis | | |
|---|---|---|---|
| | C | H | N |
| Found (%) | 65.71 | 4.27 | 3.31 |
| Calcd. (%) | 65.37 | 4.44 | 3.63 |

$^1$H-NMR (CDCl$_3$, δppm) 1.78 (mc, 4H), 2.42 (mc, 4H), 5.10 (s, 2H), 7.20 (mc, 7H)

EXAMPLE 13

Preparation of Compound No. 10

To 50 ml of acetonitrile, 0.55 g of N-(4-chloro-5-hydroxyphenyl)-3,4,5,6-tetrahydrophthalimide, 0.38 g of 4-fluoro-benzyl bromide and 0.27 g of potassium carbonate were added and the same procedure as in Example 10 was followed to obtain 0.7 g of the Compound No. 10.
Refractive Index n$_D$: 1.5730

| | Element Analysis | | |
|---|---|---|---|
| | C | H | N |
| Found (%) | 64.99 | 4.52 | 3.98 |
| Calcd. (%) | 65.37 | 4.44 | 3.63 |

$^1$H-NMR (CDCl$_3$, δppm) 1.74 (mc, 4H), 2.40 (mc, 4H), 4.92 (s, 2H), 7.10 (mc, 8H)

EXAMPLE 14

Preparation of Compound No. 11

To 50 ml of acetonitrile, 0.46 g anhydrous N-(4-chloro-2-fluoro-5-hydroxyphenyl)-3,4,5,6-tetrahydrophthalimidic acid, 0.27 g of benzyl bromide and 0.21 g of potassium carbonate were added and the same procedure as in Example 10 was followed to obtain 0.69 g of the Compound No. 11.
Refractive Index n$_D^{25}$: 1.5968

| | Element Analysis | | |
|---|---|---|---|
| | C | H | N |
| Found (%) | 65.22 | 4.58 | 3.59 |
| Calcd. (%) | 65.37 | 4.44 | 3.63 |

$^1$H-NMR (CDCl$_3$, δppm) 1.75 (mc, 4H), 2.38 (mc, 4H), 5.03 (s, 2H), 7.28 (mc, 7H)

EXAMPLE 15

Preparation of Compound No. 12

To 50 ml of acetonitrile, 1.0 g of N-(4-chloro-2-fluoro-5-hydroxyphenyl)-3,4,5,6-tetrahydrophthalimide, 0.6 g of 2-fluoro-benzyl chloride and 0.56 g of potassium carbonate were added and the same procedure as in Example 10 was followed to obtain 1.02 g of the Compound No. 12.
m.p.: 93°–95° C.

| | Element Analysis | | |
|---|---|---|---|
| | C | H | N |
| Found (%) | 62.33 | 4.06 | 3.42 |
| Calcd. (%) | 62.46 | 3.99 | 3.46 |

$^1$H-NMR (CDCl$_3$, δppm) 1.70 (mc, 4H), 2.33 (mc, 4H), 5.08 (s, 2H), 7.22 (mc, 6H)

EXAMPLE 16

Preparation of Compound No. 13

To 50 ml of acetonitrile, 0.46 g of N-(4-chloro-2-fluoro-5-hydroxyphenyl)-3,4,5,6-tetrahydrophthalimide, 0.29 g of 2-methyl-benzyl bromide and 0.21 g of potassium carbonate were added and the same procedure as in Example 10 was followed to obtain 0.67 g of the Compound No. 13.
m.p.: 135°–137° C.

| | Element Analysis | | |
|---|---|---|---|
| | C | H | N |
| Found (%) | 66.12 | 4.67 | 3.2 |
| Calcd. (%) | 66.08 | 4.78 | 3.5 |

$^1$H-NMR (CDCl$_3$, δppm) 1.82 (mc, 4H), 2.33 (s, 3H), 2.38 (mc, 4H), 5.17 (s, 2H), 7.13 (mc, 6H)

EXAMPLE 17

Preparation of Compound 15

To 50 ml of acetonitrile, 0.75 g of N-(2-bromo-4-chloro-5-hydroxyphenyl)-3,4,5,6-tetrahydrophthalimide, 0.36 g of benzyl bromide and 0.29 g of potassium carbonate were added and the same procedure as in Example 10 was followed to obtain 0.57 g of the Compound No. 15.

Refractive Index: $n_D^{25}$: 1.5839

|  | Element Analysis | | |
| --- | --- | --- | --- |
|  | C | H | N |
| Found (%) | 56.55 | 3.7 | 3.23 |
| Calcd. (%) | 56.46 | 3.83 | 3.13 |

$^1$H-NMR (CDCl$_3$, δppm) 1.67 (mc, 4H), 2.30 (mc, 4H), 5.03 (s, 2H), 7.17 (mc, 7H)

EXAMPLE 18

Preparation of Compound No 16

To 50 ml of acetic acid, 0.76 g of 3,4,5,6-tetrahydrophthalic anhydride and 1.7 g of 2-bromo-4-chloro-5-aminophenyl-2'-fluorobenzyl ether were added and the same procedure as in Example 11 was followed to obtain 1.72 g of the Compound No. 16.

m.p.: 142°–144.5° C.

|  | Element Analysis | | |
| --- | --- | --- | --- |
|  | C | H | N |
| Found (%) | 54.44 | 3.29 | 2.77 |
| Calcd. (%) | 54.27 | 3.47 | 3.01 |

$^1$H-NMR (CDCl$_3$, δppm) 1.70 (mc, 4H), 2.30 (mc, 4H), 5.10 (s, 2H), 7.19 (mc, 7H)

EXAMPLE 19

Preparation of Compound No. 17

To 50 ml of acetic acid, 0.76 g of 3,4,5,6-tetrahydrophthalic anhydride and 1.35 g of 4-chloro-2-fluoro-5-aminophenyl-(1-phenyl)-ethyl ether were added and the same procedure as in Example 11 was followed to obtain 1.25 g of the Compound No. 17.

Refractive Index: $n_D^{25}$: 1.5509

|  | Element Analysis | | |
| --- | --- | --- | --- |
|  | C | H | N |
| Found (%) | 66.06 | 4.85 | 3.44 |
| Calcd. (%) | 66.08 | 4.78 | 3.5 |

$^1$H-NMR (CDCl$_3$, δppm) 1.42 (d, 3H), 2.30 (mc, 4H), 2.35 (mc, 4H), 4.80 (q, 1H), 6.79 (mc, 7H)

EXAMPLE 20

To 50 ml of acetic acid, 0.76 g of 3,4,5,6-tetrahydrophthalic anhydride and 1.92 g of 2,4-dichloro-5-aminophenyl-(1-phenyl)-ethyl ether were added and the same procedure as in Example 11 was followed to obtain 1.48 g of the Compound No. 18.

Refractive Index: $n_D^{25}$: 1.5509

|  | Element Analysis | | |
| --- | --- | --- | --- |
|  | C | H | N |
| Found (%) | 63.65 | 4.58 | 3.27 |
| Calcd. (%) | 63.47 | 4.6 | 3.36 |

$^1$H-NMR (CDCl$_3$, δppm) 1.63 (d, 3H), 1.75 (mc, 4H), 2.33 (mc, 4H), 5.28 (q, 1H), 7.00 (mc, 7H)

EXAMPLE 21

Test for Evaluation of Effectiveness in Growth Inhibition by Soil Treatment

Paddy field soil was packed in a plastic pot with 60 cm diameter. After puddling, the seeds of weeds shown in Table 8 below were sown and one seedling of rice (variety: Yamahoshi) with 2 leaves were transplanted. The water level was kept at about 3 cm above the soil. The herbicide compositions formulated according to the above-described Formulation 3 was diluted with water and was uniformly applied to the water surface in the amount shown in Table 8. Further, for comparison, N-4-chloro-2-fluoro-5-isopropoxyphenyl)2-ethoxycarbonylcyclohexyl carboxylic acid ethyl ester (Comparative Compound D) disclosed in Japanese Patent Disclosure (Kokai) No. 33154/86 was also tested. After 20 days from the application of the herbicide, the growing conditions of the weeds and the rice were observed. The growth inhibition was rated in 6 ranks as in Example 5. The results are shown in Table 8.

TABLE 8

| Compound No. | Rate (a.i. g/10a) | Rice | Barnyard-grass | Small flower unbrellaplant | Monochoria | Annual broadleaved weeds |
| --- | --- | --- | --- | --- | --- | --- |
| 8 | 250 | 0 | 3 | 5 | 5 | 5 |
|  | 125 | 0 | 3 | 5 | 5 | 5 |
|  | 60 | 0 | 3 | 5 | 5 | 5 |
| 9 | 250 | 0 | 0 | 5 | 5 | 5 |
|  | 125 | 0 | 0 | 5 | 5 | 5 |
|  | 60 | 0 | 0 | 5 | 5 | 5 |
| 10 | 250 | 0 | 0 | 4 | 5 | 5 |
|  | 125 | 0 | 0 | 4 | 5 | 5 |
|  | 60 | 0 | 0 | 3 | 5 | 5 |
| 11 | 125 | 1 | 5 | 5 | 5 | 5 |
|  | 60 | 0 | 5 | 5 | 5 | 5 |
|  | 30 | 0 | 5 | 5 | 5 | 5 |
| 12 | 125 | 0 | 5 | 5 | 5 | 5 |
|  | 60 | 0 | 5 | 5 | 5 | 5 |
|  | 30 | 0 | 5 | 5 | 5 | 5 |
| 13 | 125 | 0 | 4 | 5 | 5 | 5 |
|  | 60 | 0 | 4 | 5 | 5 | 5 |
|  | 30 | 0 | 4 | 5 | 5 | 5 |
| 14 | 250 | 0 | 2 | 5 | 5 | 5 |
|  | 125 | 0 | 0 | 5 | 4 | 5 |

TABLE 8-continued

| Compound No. | Rate (a.i. g/10a) | Rice | Barnyard-grass | Small flower unbrellaplant | Monochoria | Annual broadleaved weeds |
| --- | --- | --- | --- | --- | --- | --- |
|  | 60 | 0 | 0 | 4 | 4 | 5 |
| 15 | 125 | 0 | 4 | 5 | 5 | 5 |
|  | 60 | 0 | 4 | 5 | 5 | 5 |
|  | 30 | 0 | 4 | 5 | 5 | 5 |
| 16 | 250 | 0 | 4 | 5 | 5 | 5 |
|  | 125 | 0 | 4 | 5 | 4 | 5 |
|  | 60 | 0 | 3 | 5 | 4 | 5 |
| 17 | 125 | 0 | 5 | 5 | 5 | 5 |
|  | 60 | 0 | 5 | 5 | 5 | 5 |
|  | 30 | 0 | 4 | 5 | 5 | 5 |
| 18 | 125 | 0 | 4 | 5 | 5 | 5 |
|  | 60 | 0 | 3 | 5 | 5 | 5 |
|  | 30 | 0 | 3 | 5 | 5 | 5 |
| Comparative Compound D | 125 | 0 | 0 | 2 | 0 | 0 |
|  | 60 | 0 | 0 | 0 | 0 | 0 |
|  | 30 | 0 | 0 | 0 | 0 | 0 |

EXAMPLE 22

Test for Evaluation of Effectiveness in Growth Inhibition by Foliage Treatment

The same procedure as in Example 5 was repeated except that the compounds tested were Compound Nos. 11-18. Further, for comparison, the Comparative Compound D described in Example 21 was also tested. The results are shown in Table 9 below.

TABLE 9

| Compound No. | Rate (a.i. g/10a) | Soybean | Wheat | Corn | Slender amaranth | Velvetleaf | Cocklebur |
| --- | --- | --- | --- | --- | --- | --- | --- |
| 11 | 125 | 1 | 0 | 1 | 5 | 5 | 5 |
|  | 60 | 1 | 0 | 0 | 5 | 5 | 5 |
|  | 30 | 0 | 0 | 0 | 5 | 5 | 5 |
| 12 | 125 | 1 | 0 | 0 | 5 | 5 | 5 |
|  | 60 | 0 | 0 | 0 | 5 | 5 | 5 |
|  | 30 | 0 | 0 | 0 | 5 | 5 | 4.5 |
| 13 | 125 | 1 | 0 | 1 | 5 | 5 | 4.5 |
|  | 60 | 0 | 0 | 0 | 5 | 4.5 | 4 |
|  | 30 | 0 | 0 | 0 | 5 | 4.5 | 3 |
| 15 | 125 | 2 | 0 | 0 | 5 | 5 | 4.5 |
|  | 60 | 1 | 0 | 0 | 5 | 4.5 | 3 |
|  | 30 | 1 | 0 | 0 | 5 | 4.5 | 3 |
| 16 | 125 | 1 | 0 | 0 | 4 | 4 | 3 |
|  | 60 | 0 | 0 | 0 | 4 | 3 | 3 |
|  | 30 | 0 | 0 | 0 | 3 | 3 | 0 |
| 17 | 125 | 3 | 2 | 1 | 5 | 5 | 5 |
|  | 60 | 3 | 2 | 1 | 5 | 5 | 5 |
|  | 30 | 2 | 1 | 0 | 5 | 5 | 4.5 |
| 18 | 125 | 1 | 0 | 0 | 5 | 5 | 4 |
|  | 60 | 1 | 0 | 0 | 5 | 5 | 4 |
|  | 30 | 1 | 0 | 0 | 3 | 5 | 4 |
| Comparative Compound D | 125 | 0 | 0 | 0 | 0 | 1 | 0 |
|  | 60 | 0 | 0 | 0 | 0 | 0 | 0 |
|  | 30 | 0 | 0 | 0 | 0 | 0 | 0 |

EXAMPLE 23

Preparation of N-(2,4-dichloro-5-(1-hydroxymethylethoxyphenyl)-3,4,5,6-tetrahydrophthalimide (Compound No. 23 (Table 4))

To 50 ml of acetic acid, 3.19 g of 3,4,5,6-tetrahydrophthalic anhydride and 4.95 g of 2-(2,4-dichloro-5-aminophenoxy)propanol were added and the mixture was heated to reflux under stirring for 16 hours. After cooling, the solvent was evaporated under reduced pressure and the residue was purified by column chromatography (silica gel, benzene/ethyl acetate=10/1 (v/v)) to obtain 1.42 g of the desired product.

Refractive Index: $n_D^{25}$ 1.5640

$^1$H-NMR (CDCl$_3$, δppm) 1.22 (3H, d), 1.43-1.92 (4H, m), 2.09-2.72 (4H, m), 3.65 (2H, d), 4.20 (1H, m), 4.37 (1H, br), 6.87 (1H, s), 7.42 (1H, s)

EXAMPLE 24

Preparation of N-(4-chloro-2-fluoro-5-(1-hydroxymethylethoxyphenyl)-3,4,5,6-tetrahydrophthalimide (Compound No. 19 (Table 4))

The same procedure as in Example 23 was repeated except that 2-(2-chloro-4-fluoro 5-aminophenoxy)-propanol was used as the aniline derivative to obtain the desired product.

Refractive Index: $n_D^{25}$ 1.5494

$^1$H-NMR (CDCl$_3$, δppm) 1.25 (3H, d), 1.47-1.94 (4H, m), 2.11-2.67 (4H, m), 3.69 (2H, d), 3.85 (1H, m), 4.33 (1H, br), 6.89 (1H, s), 7.17 (1H, s)

EXAMPLE 25

Preparation of
N-(4-chloro-2-fluoro-5-(1-acetoxymethylethoxyphenyl)-3,4,5,6-tetrahydrophthalimide (Compound No. 20 (Table 4))

The same procedure as in Example 23 was repeated except that O-acetyl derivative of 2-(2-chloro-4-fluoro-5-aminophenoxy)propanol was used as the aniline derivative to obtain the desired product.

Refractive Index: $n_D$ 1.5410

$^1$H-NMR (CDCl$_3$, δppm) 1.30 (3H, d), 1.50–1.95 (4H, m), 1.99 (3H, s), 2.17–2.63 (4H, m), 4.21 (2H, d), 4.50 (1H, br), 6.90 (1H, s), 7.18 (1H, s)

EXAMPLE 26

Preparation of
N-(4-chloro-2-fluoro-5-(2-benzyloxy-1-methylethoxyphenyl)-3,4,5,6-tetrahydrophthalimide (Compound No. 21 (Table 4))

The same procedure as in Example 23 was repeated except that 4-chloro-2-fluoro-5-(2-(1-benzyloxypropyl)oxyaniline was used as the aniline derivative to obtain the desired Refractive Index: $n_D^{25}$ 1.5508

$^1$H-NMR (CDCl$_3$, δppm) 1.28 (3H, d), 1.64–1.97 (4H, m), 2.23–2.62 (4H, m), 4.40 (2H, m), 4.50 (1H, s), 6.82–7.48 (7H, m)

EXAMPLE 27

Preparation of
N-(2,4-dichloro-5-(2-(1-(o-fluorobenzyloxy)propyl)oxy)phenyl-3,4,5,6-tetrahydrophthalimide (Compound No. 22 (Table 4))

The same procedure as in Example 23 was repeated except that 2,4-dichloro-5-(2-(1-o-fluorobenzyloxypropyl)oxy)aniline was used as the aniline derivative to obtain the desired product.

Refractive Index: $n_D^{25}$ 1.5668

$^1$H-NMR (CDCl$_3$, δppm) 1.42 (3H, d), 1.55–2.08 (4H, m), 2.17–2.70 (4H, m), 4.58 (2H, m), 4.70 (1H, m), 6.70–7.58 (6H, m)

EXAMPLE 28

Test for Evaluation of Effectiveness in Growth Inhibition by Soil Treatment

The same procedure as in Example 21 was repeated except that the compounds tested were Compound No.s 19–23. For comparison, the Comparative Compound D described in Example 21 was also tested. The results are shown in Table 10 below.

TABLE 10

| Compound No. | Rate (a.i. g/10a) | Herbicidal Effectiveness | | | | | Phytotoxicity | | |
|---|---|---|---|---|---|---|---|---|---|
| | | Barnyard-grass | Pale smartweed | Slender amaranth | Velvetleaf | Cocklebur | Soybean | Wheat | Corn |
| 19 | 30 | 5 | 5 | 5 | 5 | 5 | 2 | 0 | 0 |
|  | 15 | 4 | 5 | 5 | 5 | 5 | 2 | 0 | 0 |
| 20 | 30 | 5 | 5 | 5 | 5 | 5 | 3 | 0 | 0 |
|  | 15 | 5 | 5 | 5 | 5 | 5 | 3 | 0 | 0 |
| 21 | 30 | 5 | 5 | 5 | 5 | 4 | 3 | 0 | 0 |
|  | 15 | 5 | 5 | 5 | 4 | 3 | 3 | 0 | 0 |
| 22 | 60 | 0 | 3 | 5 | 5 | 5 | 1 | 0 | 0 |
|  | 30 | 0 | 3 | 5 | 5 | 4 | 1 | 0 | 0 |
| 23 | 60 | 0 | 4 | 5 | 5 | 5 | 1 | 0 | 0 |
|  | 30 | 0 | 4 | 5 | 5 | 4 | 1 | 0 | 0 |
| Comparative Compound D | 60 | 1 | 3 | 4 | 3 | 4 | 2 | 0 | 0 |
|  | 30 | 0 | 2 | 3 | 3 | 3 | 1 | 0 | 0 |

EXAMPLE 29

Test for Evaluation of Effectiveness in Growth Inhibition by Foliage Treatment

The same procedure as in Example 5 was repeated except that the compounds tested were Compound Nos. 19–23. Further, for comparison, the Comparative Compound D described in Example 21 was also tested. The results are shown in Table 11 below.

TABLE 11

| Compound No. | Rate (a.i. g/10a) | Herbicidal Effectiveness | | | | | Phytotoxicity Rice |
|---|---|---|---|---|---|---|---|
| | | Barnyard-grass | Small flower umbrellaplant | Bulrush | Monochoria | Annual broadleaved weeds | |
| 19 | 30 | 5 | 5 | 4 | 5 | 5 | 1 |
|  | 15 | 5 | 5 | 3 | 5 | 5 | 1 |
| 20 | 30 | 4 | 5 | 3 | 5 | 5 | 1 |
|  | 15 | 4 | 5 | 3 | 5 | 5 | 1 |
| 21 | 30 | 4 | 5 | 3 | 5 | 5 | 1 |
|  | 15 | 4 | 5 | 3 | 5 | 5 | 1 |
| 22 | 60 | 5 | 5 | 0 | 5 | 5 | 0 |
|  | 30 | 4 | 4 | 0 | 5 | 5 | 0 |
| 23 | 60 | 5 | 5 | 3 | 5 | 5 | 0 |
|  | 30 | 5 | 4 | 3 | 5 | 5 | 0 |
| Comparative Compound D | 60 | 4 | 5 | 4 | 5 | 5 | 3 |
|  | 30 | 3 | 5 | 3 | 4 | 5 | 2 |

EXAMPLE 30

Preparation of N-(4-chloro-5-hydroxymethylphenyl)-3,4,5,6-tetrahydrophthalimide (Compound No. 24 (Table 5))

To 50 ml of acetic acid, 2.47 g of 3,4,5,6-tetrahydrophthalic anhydride and 2.56 g of 4-chloro-5-hydroxymethyl aniline were added and the mixture was heated to reflux under stirring for 16 hours. After cooling, the solvent was evaporated under reduced pressure and the residue was purified by column chromatography (silica gel, benzene/ethyl acetate=10/1 (v/v)) to obtain 1.82 g of the desired product.

m.p.: 77°–79° C.

$^1$H-NMR (CDCl$_3$, δppm) 1.52–1.98 (4H, m), 2.18–2.61 (4H, m), 3.08 (1H, s), 4.72 (2H, s), 6.95–7.57 (3H, m)

EXAMPLE 31

Preparation of N-(2-fluoro-4-chloro-5-cyanophenyl)-3,4,5,6-tetrahydrophthalimide (Compound No. 30 (Table 5))

To 30 ml of thionyl chloride, 1.13 g of N-(2-fluoro-4-chloro-5-aminocarbonylphenyl)-3,4,5,6-tetrahydrophthalimide was added and the mixture was heated to reflux under stirring for 16 hours. After cooling, the solvent was evaporated under reduced pressure and the residue was purified by column chromatography (silica gel, benzene/ethyl acetate=10/1 (v/v)) to obtain 0.63 g of the desired product. m.p.: 160°–162° C.

$^1$H-NMR (CDCl$_3$, δppm) 1.67–2.10 (4H, m), 2.20–2.70 (4H, m), 7.40 (1H, d), 7.60 (1H, d)

EXAMPLE 32

Preparation of Compound No. 25 (Table 5)

The same procedure as in Example 30 was repeated except that 4-chloro-5-((acetyloxy)methyl]aniline was used as the aniline derivative to obtain the Compound No. 25.

m.p.: 100°–101° C.

$^1$H-NMR (CDCl$_3$, δppm) 1.52–2.03 (4H, m), 2.13 (3H, s), 2.22–2.72 (4H, m), 5.22 (2H, s), 7.03–7.58 (3H, m)

EXAMPLE 33

Preparation of Compound No. 26 (Table 5)

The same procedure as in Example 30 was repeated except that 4-chloro-5-[[1-(ethoxycarbonyl)ethoxy)methyl]aniline was used as the aniline derivative to obtain the Compound No. 26.

m.p.: 77°–79° C.

$^1$H-NMR (CDCl$_3$, δppm) 1.50–1.96 (4H, m), 2.17–2.65 (4H, m), 4.72 (4H, s), 6.78–7.67 (7H, m)

EXAMPLE 34

Preparation of Compound No. 27 (Table 5)

The same procedure as in Example 30 was repeated except that 4-chloro-5-[[1-(ethoxycarbonyl)ethoxy]methyl]aniline was used as the aniline derivative to obtain the Compound No. 27.

Refractive Index: n$_D^{25}$ 1.5512

$^1$H-NMR (CDCl$_3$, δppm) 1.42 (3H, t), 1.62–2.07 (4H, m), 2.15–2.65 (4H, m), 4.22 (4H, q), 4.70 (2H, s), 7.00–7.63 (3H, m)

EXAMPLE 35

Preparation of Compound No. 28 (Table 5)

The same procedure as in Example 31 was repeated except that N-(4-chloro-5-aminocarbonylphenyl)-3,4,5,6-tetrahydrophthalimide was used to obtain the Compound No. 28.

m.p.:135°–137° C.

$^1$H-NMR (CDCl$_3$, δppm) 1.58–2.03 (4H, m), 2.15–2.72 (4H, m), 7.27–7.83 (3H, m)

EXAMPLE 36

Preparation of Compound No. 29 (Table 5)

The same procedure as in Example 31 was repeated except that N-(4-bromo-5-aminocarbonylphenyl)-3,4,5,6-tetrahydrophthalimide was used to obtain the Compound No. 29.

m.p.:151°–153° C.

$^1$H-NMR (CDCl$_3$, δppm) 1.62–2.11, (4H, m), 2.18–2.76 (4H, m), 7.37–7.93 (3H, m)

EXAMPLE 37

Preparation of Compound No. 31 (Table 5)

The same procedure as in Example 31 was repeated except that N-(4-trifluoromethyl-5-aminocarbonylphenyl)-3,4,5,6-tetrahydrophthalimide was used to obtain the Compound No. 31.

m.p.: 211°–214° C.

$^1$H-NMR (CDCl$_3$, δppm) 1.58–2.05 (4H, m), 2.23–2.80 (4H, m), 7.57–8.07 (3H, m)

EXAMPLE 38

Test for Evaluation of Effectiveness in Growth Inhibition by Soil Treatment

The same procedure as in Example 21 was repeated except that the compounds tested were Compound Nos. 24–30. For comparison, the Comparative Compound A described in Example 5 was also tested. The results are shown in Table 12 below.

TABLE 12

| Compound No. | Rate (a.i. g/10a) | Herbicidal Effectiveness | | | Phytotoxicity Rice |
|---|---|---|---|---|---|
| | | Small flower umbrellaplant | Monochoria | Annual broadleaved weeds | |
| 24 | 60 | 5 | 5 | 5 | 0 |
| | 30 | 4 | 5 | 5 | 0 |
| 25 | 125 | 5 | 5 | 5 | 0 |
| | 60 | 5 | 4 | 5 | 0 |
| 26 | 30 | 5 | 5 | 3 | 0 |
| | 15 | 5 | 5 | 3 | 0 |
| 27 | 125 | 4 | 5 | 5 | 0 |
| | 60 | 4 | 4 | 4 | 0 |
| 28 | 30 | 5 | 5 | 5 | 0 |
| | 15 | 5 | 5 | 5 | 0 |

TABLE 12-continued

| Compound No. | Rate (a.i. g/10a) | Herbicidal Effectiveness | | | Phytotoxicity Rice |
|---|---|---|---|---|---|
| | | Small flower umbrellaplant | Monochoria | Annual broadleaved weeds | |
| 29 | 30 | 5 | 5 | 5 | 0 |
| | 15 | 5 | 5 | 5 | 0 |
| Comparative Compound A | 60 | 5 | 5 | 5 | 3 |
| | 30 | 5 | 4 | 5 | 2 |

EXAMPLE 39

Test for Evaluation of Effectiveness in Growth Inhibition by Foliage Treatment

The same procedure as in Example 5 was repeated except that the compounds tested were Compound Nos. 24, 25, 27-31. Further, for comparison, the Comparative Compound A described in Example 5 was also tested. The results are shown in Table 13 below.

TABLE 13

| Compound No. | Rate (a.i g/10a) | Herbicidal Effectiveness | | | | Phytotoxicity | | |
|---|---|---|---|---|---|---|---|---|
| | | Pale smartweed | Slender amaranth | Velvetleaf | Cocklebur | Soybean | Wheat | Corn |
| 24 | 60 | 3 | 5 | 5 | 5 | 1 | 0 | 0 |
| | 30 | 3 | 5 | 5 | 4 | 1 | 0 | 0 |
| 25 | 60 | 3 | 5 | 5 | 4 | 0 | 0 | 0 |
| | 30 | 3 | 4 | 5 | 4 | 0 | 0 | 0 |
| 27 | 30 | 5 | 5 | 5 | 5 | 2 | 0 | 0 |
| | 15 | 5 | 5 | 5 | 5 | 1 | 0 | 0 |
| 28 | 60 | 4 | 5 | 5 | 5 | 1 | 0 | 0 |
| | 30 | 4 | 5 | 5 | 4 | 1 | 0 | 0 |
| 29 | 125 | 3 | 5 | 5 | 4 | 0 | 0 | 0 |
| | 60 | 3 | 5 | 5 | 4 | 0 | 0 | 0 |
| 30 | 30 | 5 | 5 | 5 | 5 | 1 | 0 | 0 |
| | 15 | 5 | 5 | 5 | 5 | 1 | 0 | 0 |
| 31 | 30 | 5 | 5 | 5 | 5 | 2 | 1 | 0 |
| | 15 | 5 | 5 | 5 | 5 | 2 | 0 | 0 |
| Comparative Compound A | 60 | 3 | 4 | 3 | 4 | 2 | 0 | 0 |
| | 30 | 2 | 3 | 3 | 3 | 1 | 0 | 0 |

We claim:

1. A tetrahydrophthalimide derivative of the formula (I):

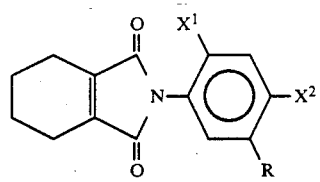

wherein $X^1$ is fluorine and $X^2$ represents halogen, hydrogen or trifluoromethyl; R represents:

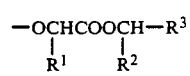

wherein $R^1$ and $R^2$, which may be the same or different, represent hydrogen or methyl, $R^3$ represents 2-tetrahydrofurfuryl or 3-methyl-1,2,4-oxadizol-5-yl;

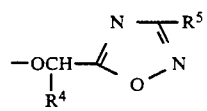

wherein $R^4$ is hydrogen or methyl, $R^5$ is methyl or benzyl;

wherein $R^8$ is hydrogen, acyl or arylalkyl, or a $C_1$-$C_4$ alkyl substituted with an alkoxycarbonyl group.

2. The tetrahydrophthalimide derivative of claim 1, which is represented by the formula:

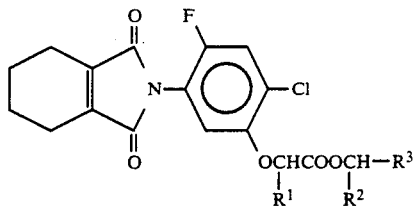

wherein $R^1$, $R^2$ and $R^3$ represent the same meaning as in claim 1.

3. The tetrahydrophthalimide derivative of claim 1, which is represented by the formula:

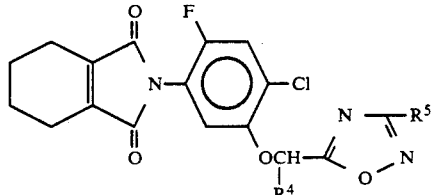

wherein $R^4$ and $R^5$ represent the same meaning as in claim 1.

4. The tetrahydrophthalimide derivative of claim 1, which is represented by the formula:

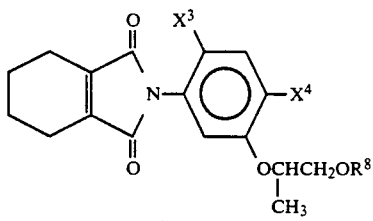

[V]

wherein $X^3$ and $X^4$, the same or different, represent halogen, $R^8$ represent the same meaning as in claim 1.

5. A herbicide composition comprising a herbicidal effective amount of the tetrahydrophthalimide derivative of claim 1 in an agriculturally acceptable carrier.

6. The herbicide composition of claim 5, which comprises a herbicidal effective amount of the tetrahydrophthalimide derivative of claim 2 in an agriculturally acceptable carrier.

7. The herbicide composition of claim 5, which comprises a herbicidal effective amount of the tetrahydrophthalimide derivative of claim 3 in an agriculturally acceptable carrier.

8. The herbicide composition of claim 5, which comprises a herbicidal effective amount of the tetrahydrophthalimide derivative of claim 5 in an agriculturally acceptable carrier.

* * * * *